US009092389B2

(12) United States Patent
Klemm et al.

(10) Patent No.: US 9,092,389 B2
(45) Date of Patent: *Jul. 28, 2015

(54) ADVANCED AVAILABILITY DETECTION

(75) Inventors: Reinhard Peter Klemm, Basking Ridge, NJ (US); Lynne Shapiro Brotman, Westfield, NJ (US)

(73) Assignee: Avaya Inc., Basking Ridge, NJ (US)

( * ) Notice: Subject to any disclaimer, the term of this patent is extended or adjusted under 35 U.S.C. 154(b) by 791 days.

This patent is subject to a terminal disclaimer.

(21) Appl. No.: 12/645,871

(22) Filed: Dec. 23, 2009

(65) Prior Publication Data

US 2010/0232587 A1      Sep. 16, 2010

Related U.S. Application Data

(60) Provisional application No. 61/160,572, filed on Mar. 16, 2009.

(51) Int. Cl.
| H04M 3/42 | (2006.01) |
| G06F 15/173 | (2006.01) |
| A61K 9/51 | (2006.01) |
| A61K 47/42 | (2006.01) |
| G06F 9/54 | (2006.01) |
| G06Q 10/06 | (2012.01) |
| G06Q 10/10 | (2012.01) |
| H04L 29/08 | (2006.01) |

(52) U.S. Cl.
CPC ........ *G06F 15/17306* (2013.01); *A61K 9/5169* (2013.01); *A61K 47/42* (2013.01); *G06F 9/54* (2013.01); *G06Q 10/06* (2013.01); *G06Q 10/107* (2013.01); *H04L 67/22* (2013.01); *H04L 67/24* (2013.01)

(58) Field of Classification Search
USPC ........................................ 379/201.01, 201.04
See application file for complete search history.

(56) References Cited

U.S. PATENT DOCUMENTS

| 6,128,646 | A | 10/2000 | Miloslavsky |
| 7,177,316 | B1 | 2/2007 | Pilecek |
| 7,277,384 | B1 * | 10/2007 | Chan et al. ................ 370/230 |
| 7,424,537 | B2 | 9/2008 | Bennett et al. |
| 7,529,683 | B2 | 5/2009 | Horvitz et al. |

(Continued)

FOREIGN PATENT DOCUMENTS

| CN | 1901513 A | 1/2007 |
| CN | 1992654 | 7/2007 |

(Continued)

OTHER PUBLICATIONS

Noll, Joachim, PCT Application No. PCT/US2010/027396 Jun. 11, 2010, , Publisher: PCT, Published in: PCT.

(Continued)

*Primary Examiner* — William Deane, Jr.

(57) ABSTRACT

A method is provided in which determines user availability on the basis of the manner in which a person uses a computing device that is associated with a telecommunications terminal. Specifically, the present invention is for a method in which a telecommunications terminal determines whether its user is available to accept an incoming invitation to participate in a telecommunications session based on: (1) a characteristic of the use of a software application, (2) a characteristic of the use of a resource of a terminal, (3) a sensor input, (4) a characteristic of the incoming invitation or (5) any combination of (1), (2), (3), (4), and (5).

20 Claims, 13 Drawing Sheets

(56) References Cited

U.S. PATENT DOCUMENTS

| | | | |
|---|---|---|---|
| 7,603,464 B2 * | 10/2009 | White | 709/226 |
| 7,613,589 B2 * | 11/2009 | Hosagrahara | 702/182 |
| 7,689,426 B2 * | 3/2010 | Matula | 704/270.1 |
| 7,689,657 B2 | 3/2010 | Daniell et al. | |
| 7,693,509 B2 | 4/2010 | Miyata | |
| 7,958,453 B1 | 6/2011 | Taing | |
| 7,970,384 B1 | 6/2011 | Lambert et al. | |
| 8,082,302 B2 | 12/2011 | Becker et al. | |
| 8,190,705 B2 | 5/2012 | Bennett et al. | |
| 8,294,600 B2 * | 10/2012 | Peterson et al. | 341/27 |
| 8,358,762 B1 | 1/2013 | Renner et al. | |
| 8,589,140 B1 * | 11/2013 | Poulin | 703/22 |
| 2002/0059577 A1 * | 5/2002 | Lu et al. | 725/9 |
| 2004/0143603 A1 | 7/2004 | Kaufmann et al. | |
| 2005/0198321 A1 * | 9/2005 | Blohm | 709/228 |
| 2006/0004911 A1 | 1/2006 | Becker et al. | |
| 2006/0015609 A1 | 1/2006 | Hagale et al. | |
| 2006/0067250 A1 * | 3/2006 | Boyer et al. | 370/260 |
| 2006/0072721 A1 | 4/2006 | Wisniewski | |
| 2006/0253593 A1 * | 11/2006 | Jachner | 709/227 |
| 2007/0004385 A1 | 1/2007 | Horvitz et al. | |
| 2007/0061347 A1 * | 3/2007 | Burnley et al. | 707/100 |
| 2007/0081651 A1 * | 4/2007 | Iyer et al. | 379/202.01 |
| 2007/0130260 A1 | 6/2007 | Weintraub et al. | |
| 2007/0143472 A1 | 6/2007 | Clark et al. | |
| 2007/0186007 A1 | 8/2007 | Field et al. | |
| 2008/0019292 A1 | 1/2008 | John et al. | |
| 2008/0125184 A1 | 5/2008 | Sano | |
| 2008/0133742 A1 | 6/2008 | Southiere et al. | |
| 2008/0240384 A1 | 10/2008 | Suryanarayana et al. | |
| 2008/0261630 A1 | 10/2008 | Wormald et al. | |
| 2008/0281783 A1 | 11/2008 | Papkoff et al. | |
| 2009/0216725 A1 | 8/2009 | Yaqub | |
| 2010/0306327 A1 * | 12/2010 | Shinkawa et al. | 709/206 |
| 2013/0041953 A1 | 2/2013 | Renner et al. | |

FOREIGN PATENT DOCUMENTS

| | | |
|---|---|---|
| EP | 1505529 A1 | 2/2005 |
| EP | 2141901 | 1/2010 |
| FR | 2814022 | 3/2002 |
| JP | H11-331369 | 11/1999 |
| JP | 2003-114858 | 4/2003 |
| JP | 2003-271204 | 9/2003 |
| JP | 2005-045724 | 2/2005 |
| JP | 2005-110026 | 4/2005 |
| JP | 2005-110028 | 4/2005 |
| JP | 2005-136845 | 5/2005 |
| JP | 2005-268954 | 9/2005 |
| JP | 2006-119415 | 8/2006 |
| JP | 2006-229415 | 8/2006 |
| JP | 2006-333040 | 12/2006 |
| JP | 2008-118409 | 5/2008 |
| JP | 2008-160753 | 7/2008 |
| JP | 2008-182465 | 8/2008 |
| WO | WO 98/35482 | 8/1998 |
| WO | 0169432 A2 | 9/2001 |
| WO | WO 2006/080068 | 8/2006 |

OTHER PUBLICATIONS

Wheeler, Owen, GB Application No. GB1004182.0 Office Action Jul. 16, 2010, , Publisher: UK IPO, Published in: GB.

Wheeler, Owen, GB Application No. GB1004183.8 Office Action Jul. 16, 2010, , Publisher: UK IPO, Published in: GB.

* cited by examiner

ADVANCED AVAILABILITY DETECTION

CROSS-REFERENCE TO RELATED APPLICATIONS

This application claims the benefit of U.S. provisional application Ser. No. 61/160,572, filed Mar. 16, 2009, entitled Presence Based on the Context or Persona of the Party Being Contacted, which is also incorporated by reference.

FIELD OF THE INVENTION

The present invention relates to telecommunications in general, and, more particularly, to availability detection.

BACKGROUND OF THE INVENTION

The term "availability" in the context of telecommunications refers to whether a user is available to accept incoming invitations to participate in telecommunications sessions. For example, a user may be unavailable to accept telephone calls if the telephone line is busy. In instant messaging, a user is unavailable if the user's online status is set to "busy." In the latter case, online status is set manually through a "Change Online Status" menu which is commonly available in instant messaging clients.

Telecommunications devices use availability information to decide whether to accept incoming telecommunications, alert users of incoming telecommunications, display incoming telecommunications, and other purposes. Availability detection, as implemented in existing applications, reflects either the utilization of telecommunications channels or the express unwillingness of users to participate in telecommunications.

At present, availability detection suffers from at least two drawbacks. First, the "availability" of a user reflects only the user's preferences; it does not account for situations in which a user's availability needs to reflect the preferences of third parties. For instance, in the employment setting, it is desirable for both employees, as well as employers to have a say whether the employees are available. Second, users often forget to manually reset their online status, and consequently, it is difficult to know when one's online status is a true reflection of his or her availability.

Therefore, the need exists for a method which addresses these drawbacks to provide improved and more robust telecommunications devices.

SUMMARY OF THE INVENTION

The present invention addresses the drawbacks of the prior art by providing a method that determines user availability on the basis of the manner in which a person uses a computing device that is associated with a telecommunications terminal.

More specifically, the present invention is for a method in which a telecommunications terminal determines whether its user is available to accept an incoming invitation to participate in a telecommunications session based on:
  (1) a characteristic of the use of a software application, or
  (2) a characteristic of the use of a resource of a terminal, or
  (3) a sensor input, or
  (4) a characteristic of the incoming invitation, or
  (5) any combination of (1), (2), (3) and (4).

For example, and without limitation, in one embodiment of the present invention, the office telephone and office desktop computer of a user are associated with each other. When a call is received at the office telephone, the present invention obtains information about the use of the desktop computer. Based on this information, the embodiment of present invention determines whether the user is available to accept the incoming call.

Additionally, the present invention, in some of its embodiments, provides a method for the centralized enforcement of availability policies. For the purposes of this specification, the term "availability policy" is defined as a set of one or more rules which determine when a user is available for telecommunications.

In a first embodiment of the present invention, user availability is determined according to a characteristic of the use of a software application that is running on a computing device. The computing device is associated with a telecommunications terminal at which an invitation to participate in a telecommunications session is received.

For the purposes of this specification, the term "characteristic of the use of a software application" is defined as any item of information concerning the manner in which a specific software application is used.

In one instance of its first embodiment, the present invention determines availability based on one or more web sites that have been visited by a web browser running on a user's desktop computer. In accordance with this embodiment of the present invention, the websites serve as a clue whether the user is available to accept invitations for telecommunications sessions. For example, if the user visits entertainment web sites such as Movies.com™, this is an indication that the user browsing the Internet for personal entertainment and not in relation to the user's employment. In accordance with the availability policy of this example, when a user is found to be visiting Movies.com™, the user is considered available to participate in telecommunications.

In another instance of its first embodiment, the present invention identifies one or more keywords which are typed in documents that are open for editing on the user's desktop computer. In accordance with this embodiment, the keywords serve as a basis for determining whether the user is available to take part in telecommunications. For example, and without limitation, if an open document contains Internet slang words, this is an indication that the user is engaged in a personal conversation and not in employment-related matters. Thus, in accordance with the availability policy of this example, when Internet slang words are identified in a document, the user is considered available to participate in telecommunications.

In general, the policies of the above examples consider a user available when the user is not engaged in an employment-related activity. Although, the rationale behind the policies is increasing employee productivity, the scope of the present invention is not limited to any particular set of policies. The policies which the present invention implements are determined by the needs of the users of the invention.

In accordance with a second embodiment of the present invention, a measurement of the use of a resource of a computing device is obtained. For the purposes of this specification, the term "characteristic of the use of a resource of a computing device" is defined as any information concerning at least one of: (1) whether a particular hardware component or peripheral device of the computing device is used at all; (2) the load and/or utilization rate of a hardware component of the computing device; and (3) the load and/or utilization rate of a peripheral device (e.g. a printer) that is connected to the computing device;.

In one instance of its second embodiment, the present invention determines availability on the basis of a keystroke rate. In accordance with the availability policy of this embodiment, all incoming invitations to the user to participate in a telecommunications session are declined when the user's keystroke rate exceeds a particular threshold of keystrokes per unit time. The rationale for this policy is that if a user is typing fast, the user is most likely devoting his full attention to preparing a document and he or she is unwilling to be disturbed by incoming telecommunications.

In a second instance of its second embodiment, the present invention determines availability on the basis of a cache miss rate. In accordance with the availability policy of this embodiment, all incoming invitations to the user to participate in a telecommunications session are declined when the cache miss pattern is similar to a cache miss pattern that is specified in an availability policy. The cache miss rate provides information about the type of activity in which the user of a telecommunications terminal is engaged. For example, when a user generates many cache misses, the user is likely engaged in manipulating a large data set, such as a large spreadsheet. In this example, when there are indications that a user is involved in work with spreadsheets, the user is unavailable for incoming telecommunications. Just like the exemplary policies described with respect to the first embodiment, the rule of this example promotes increased employee productivity by ensuring that people are not disturbed when their use of computing resources indicates that they are engaged in a productive activity.

In a third embodiment of the present invention, availability is determined on the basis of a characteristic of the incoming invitation to participate in a telecommunications session. For the purposes of this disclosure, the term "characteristic of an invitation to participate in a telecommunications session" is defined as at least one of (1) information about the user initiating the telecommunications session, (2) topic of the telecommunications session, (3) expected duration of the telecommunications session, and (4) priority rating for the telecommunications session.

It is to be understood, that the above embodiments and their instances are provided to better illustrate different aspects of the present invention. They are in no way exhaustive of the full scope of the invention. The following disclosure teaches examples of some embodiments of the present invention in detail.

DETAILED DESCRIPTION

Figure 1:
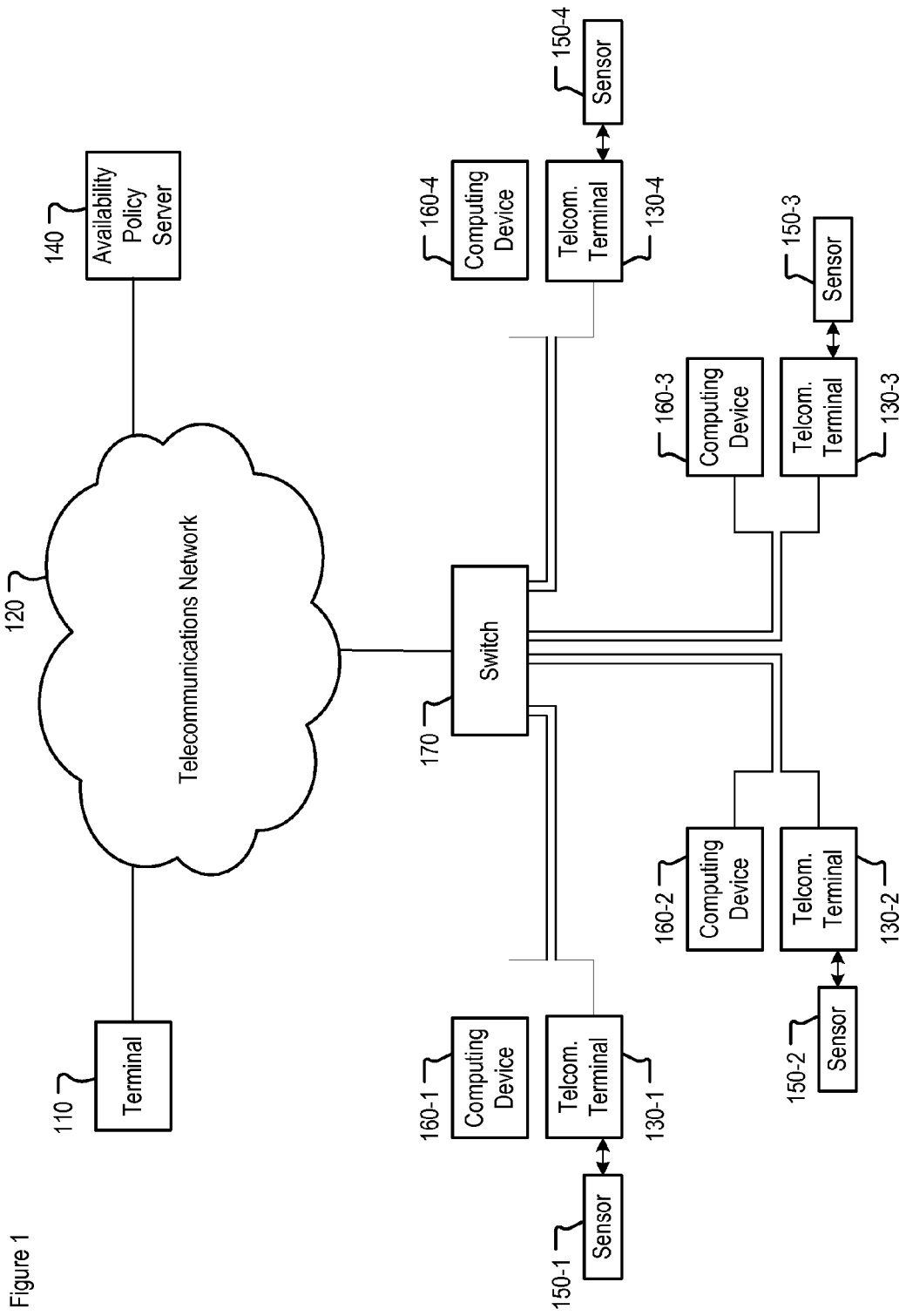
FIG. 1 depicts a schematic diagram of the salient components of the illustrative embodiment of the present invention.

FIG. 1 depicts a schematic diagram of the salient components of the illustrative embodiment of the present invention. The illustrative embodiment comprises terminal 110, telecommunications network 120, switch 170, policy server 140, sensor 150-$i$, terminal 130-$i$, and computing device 160-$i$, where $i \in \{1, 2, 3, \text{and } 4\}$.

Terminal 110 is a desk set telephone receiver. In accordance with the illustrative embodiment of the present invention, terminal 110 is capable of both voice and video telecommunications, but it will be clear to those skilled in the art, after reading this disclosure, how to make and use alternative embodiments of the present invention in which terminal 110 has only a voice capability. Furthermore, it will be clear to those skilled in the art, after reading this disclosure, how to make and use alternative embodiments of the present invention in which terminal 110 is another telecommunications device (e.g. soft phone, cellular telephone, 2-way radio, portable digital assistant, etc.).

Telecommunications network 120 transports signals between terminal 110, switch 170, computing device 160-$i$, and policy server 140. In accordance with the illustrative embodiment of the present invention, telecommunications network 120 is the Internet, but it will be clear to those skilled in the art, after reading this disclosure, how to make and use alternative embodiments of the present invention in which telecommunications network 120 is any type of telecommunications network (e.g. local area network, the Public Switched Telephone Network, SONET, ATM, cellular network, etc.).

Computing device 160-$i$ is a desktop computer that is executing one or more applications, such as, for example, and without limitation, a media player, word processor, spreadsheet software, and others. In accordance with the illustrative embodiment of the present invention, computing device 160-$i$ is a desktop computer, but it will be clear to those skilled in the art, after reading this disclosure, how to make and use alternative embodiments of the present invention in which computing device 160-$i$ is any type of computing device, such as, for example, and without limitation, a cellular telephone, personal digital assistant, smart phone, and others. Computing device 160-$i$ is further described in the discussion with respect to FIG. 2.

Terminal 130-$i$ is a telecommunications terminal. In accordance with the illustrative embodiment of the present invention, terminal 130-$i$ is capable of conducting both audio and video telephone calls, but it will be clear to those skilled in the art, after reading this disclosure, how to make and use alternative embodiments of the present invention in which terminal 130-$i$ has only a voice capability. Furthermore, it will be clear to those skilled in the art, after reading this disclosure, how to make and use alternative embodiments of the present invention in which terminal 130-$i$ is any type of telecommunications device (e.g. cellular telephone, 2-way radio, portable digital assistant, desk set telephone receiver, etc.).

Policy server 140 is a server which stores availability policy rules. In accordance with the illustrative embodiment of the present invention, terminal 130-*i* receives availability policy rules from policy server 140. However, it will be clear to those skilled in the art, after reading this disclosure, how to make and use alternative embodiments of the present invention in which terminal 130-*i* obtains the availability policy rules from another source (e.g. the rules are loaded manually on the terminal by an administrator or by the user of terminal 130-*i*, etc.). Furthermore, in accordance with the illustrative embodiment of the present invention, the availability policy rules stored at policy server 140 are specified by the user of terminal 130-*i*, but it will be clear to those skilled in the art, after reading this disclosure, how to make and use alternative embodiments of the present invention in which the availability policy rules are specified by a network administrator, or by the designers of availability detector 237.

Sensor 150-*i* is a plurality of sensors that are capable of supplying data to terminal 130-*i*. Although, in accordance with the illustrative embodiment of the present invention, sensor 150-*i* is a collection of three sensors, it will be clear to those skilled in the art, after reading this disclosure, how to make and use alternative embodiments of the present invention in which sensor 150-*i* includes any number of sensors (e.g. 1, 2, 5, 10, 15, etc.). Sensor 150-*i* is further described in the discussion with respect to FIG. 2.

Switch 170 is a network switch. In accordance with the illustrative embodiment of the present invention, switch 170 connects telecommunications network 120 to terminal 130-*i* and 160-*i*. However, it will be clear to those skilled in the art, after reading this disclosure, how to make and use alternative embodiments of the present invention in which switch 170 connects terminal 130-*i* to a telephone network such as the public switched telephone network (PSTN) and computing device 160-*i* to a data network, such as the Internet or a local area network (LAN). It will be clear to those skilled in the art, after reading this disclosure, how to make and use alternative embodiments of the present invention in which switch 170 is any type of network node (e.g. a bridge, gateway, etc.).

In accordance with the illustrative embodiment of the present invention, computing device 160-1 is associated with terminal 130-1. More specifically, the association is maintained by means of a table that relates the computing device with the terminal. In accordance with the illustrative embodiment of the present invention, the table relates the media access control (MAC) numbers of the devices, but it will be clear to those skilled in the art, after reading this disclosure, make and use alternative embodiments of the present invention in which the table relates any type of identifiers for the devices (e.g. user-assigned device names, IP addresses, network addresses, etc.). Furthermore, it will be clear to those skilled in the art, after reading this disclosure, how to make and use alternative embodiments of the present invention in which the association between the device is derivative from an association between the ports on a switch to which the devices are connected (i.e. the table relates the numbers of ports on switch 170, rather than specific devices).

Additionally, in accordance with the illustrative embodiment of the present invention, the table is stored at switch 170, however it will be clear to those skilled in the art, after reading this disclosure, how to make and use alternative embodiments of the present invention in which the table is stored elsewhere (e.g. computing device 160, policy server 140, terminal 130-1, etc.).

Figure 2:
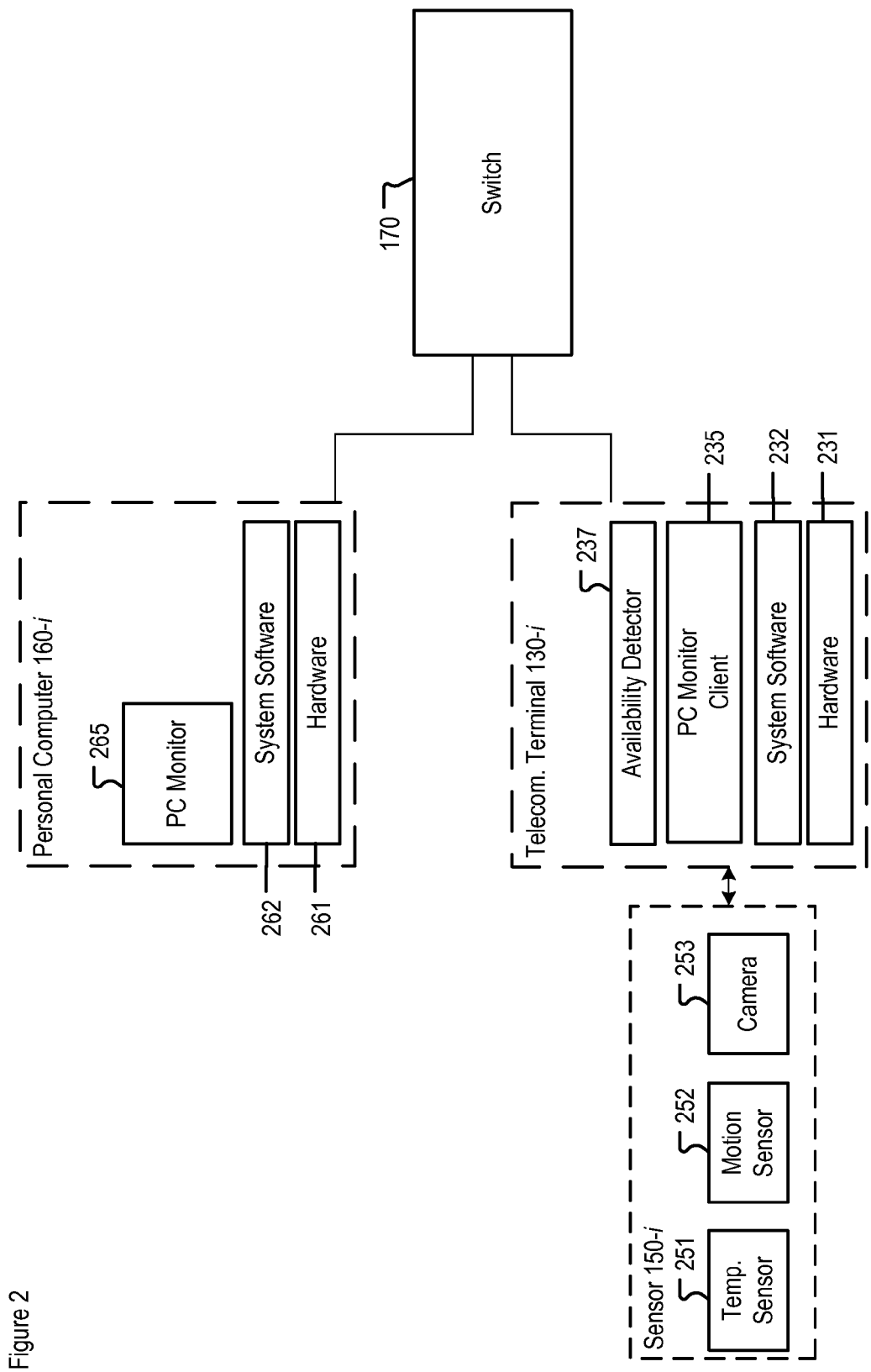
FIG. 2 depicts a schematic diagram of the salient components of the illustrative embodiment of the present invention.

FIG. 2 depicts a schematic diagram of the salient components of the illustrative embodiment of the present invention. The illustrative embodiment comprises sensor 150-*i*, terminal 130-*i*, computing device 160-*i*, temperature sensor 251, motion sensor 252, camera 253, hardware 231, system software 232, computing device monitor client 235, availability detector 237, hardware 261, system software 261, and computing device monitor 265.

Telecommunications terminal 130-*i* comprises hardware 231, system software 232, computing device monitor client 235, and availability detector 237.

Hardware 231 is the electronic components that comprise terminal 130-*i*, such as, for example, and without limitation, processor (single-core or multi-core), memory, transceiver, network interface, display, sound interface, video interface, etc. Hardware 231 is capable of executing system software and one or more applications. In accordance with the illustrative embodiment of the present invention, hardware 231 is executing computing device monitor client 235, and system software 232. It will be clear to those skilled in the art how to make and use hardware 231.

System software 232 is an operating system instance that is executing on hardware 231.

Computing device monitor client 235 is software that is capable of connecting to computing device monitor 265 and obtaining information about at least one of a characteristic of the use of a software application component that is running on computing device 160-*i* and a measurement of the use of one or more resources of computing device 160-*i*.

Availability detector 237 is software for determining whether the user of terminal 130-1 is available to participate in a telecommunications session. The operation of availability detector 237 is further described in the discussion of FIGS. 7-13.

Computing device 160-*i* comprises hardware 261, system software 262, and computing device monitor 265.

Hardware 261 is the electronic components that comprise computing device 160-*i*, such as, for example, and without limitation, processor (single-core or multi-core), memory, transceiver, network interface, display, sound interface, video interface, etc. Hardware 261 is capable of executing system software and one or more applications. In accordance with the illustrative embodiment of the present invention hardware 261 is executing computing device monitor 265 and system software 262. It will be clear to those skilled in the art how to make and use hardware 261.

System software 262 is an operating system instance that is executing on hardware 261.

Computing device monitor 265 is software for obtaining information about computing device 160-*i*. In accordance with the illustrative embodiment of the present invention, computing device monitor performs at least one of two functions:
 i. Obtaining one or more characteristics of the use of a software application component that is running on computing device 160-*i*.
 ii. Obtaining a measurement of the use of one or more resources of computing device 160-*i*.

Figure 4:
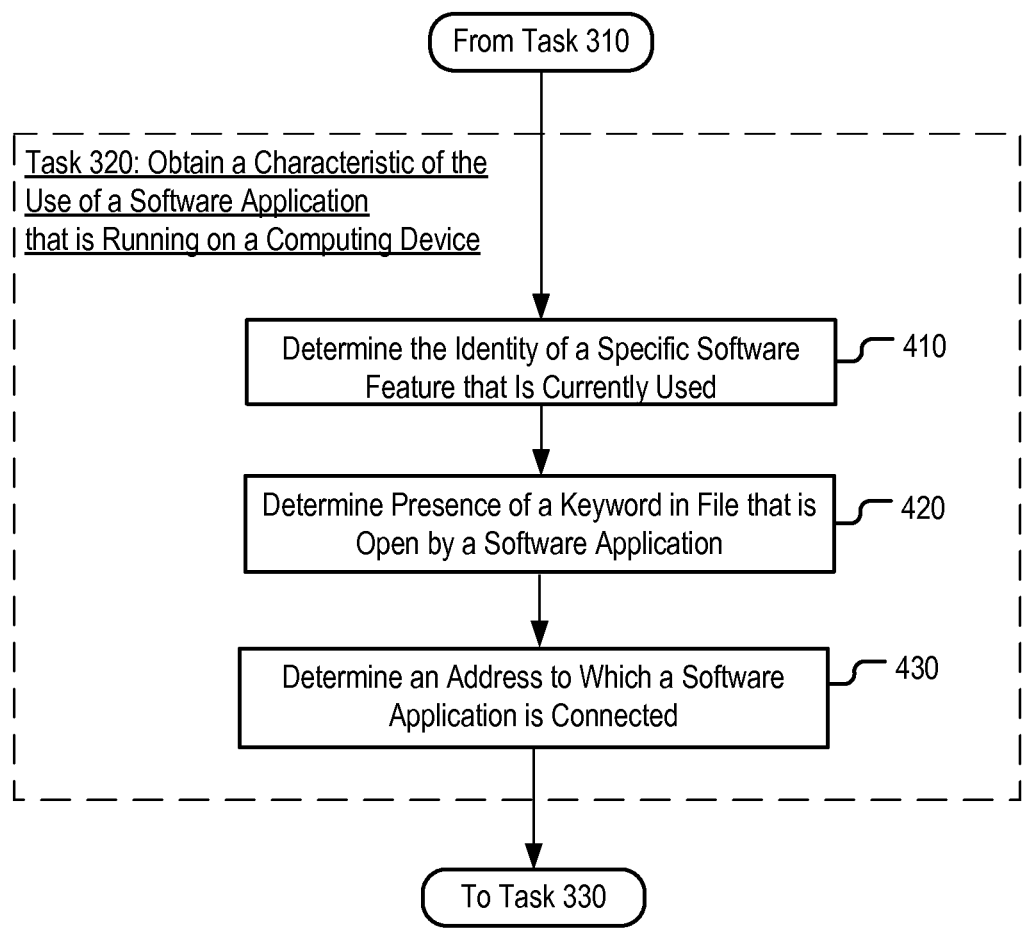
FIG. 4 depicts a flowchart of the execution of the salient subtasks associated with the performance of task 320.

The operation of computing device monitor 265 is described in further detail in the discussion with respect to FIG. 4.

Sensor 150-*i* comprises temperature sensor 251, motion sensor 252, and camera 253.

Temperature sensor 251 is a temperature sensor.

Motion sensor 252 is a motion sensor. In accordance with the illustrative embodiment of the present invention, sensor 252 is an electronic motion detector that uses infra red (IR) technology. However, it will be clear to those skilled in the art, after reading this disclosure, how to make and use alternative embodiments of the present invention in which other sensors are used (e.g. ultrasonic, microwave, hall effect, etc.).

Camera 253 is a video camera. However, it will be clear to those skilled in the art, after reading this disclosure, how to make and use alternative embodiments of the present invention in which camera 253 is a still image camera.

Figure 3:
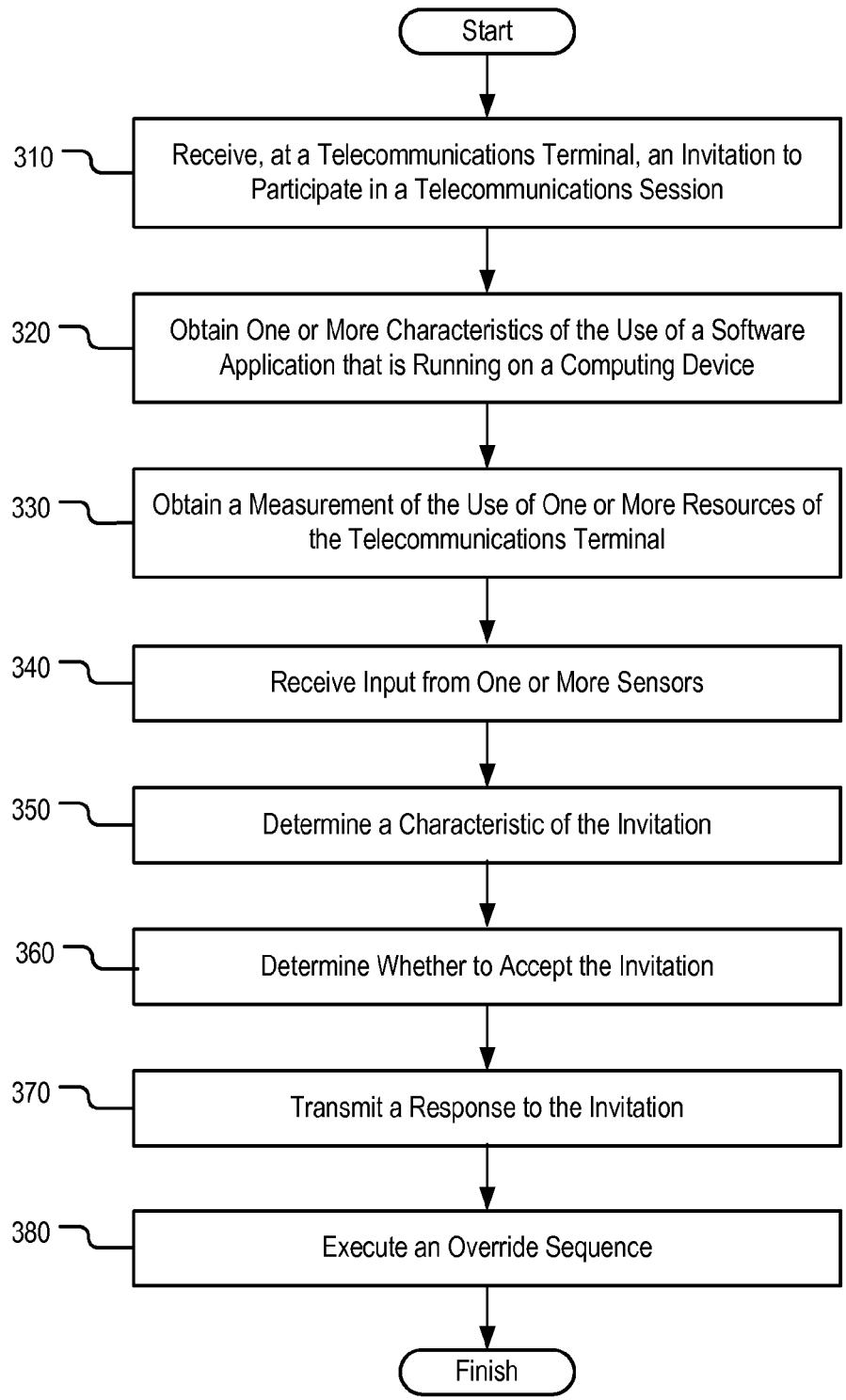
FIG. 3 depicts a flowchart of the execution of the salient tasks associated with the operation of the illustrative embodiment of the present invention.

FIG. 3 depicts a flowchart of the execution of the salient tasks associated with the operation of the illustrative embodiment of the present invention. It will be clear to those skilled in the art, after reading this disclosure, how to perform the tasks associated with FIG. 3 in a different order than represented or to perform one or more of the tasks concurrently. Furthermore, it will be clear to those skilled in the art, after reading this disclosure, how to make and use alternative embodiments of the present invention that omit one or more of the tasks.

At task 310, terminal 130-1 receives an invitation to participate in a telecommunications session. The invitation is transmitted from terminal 110. In accordance with the illustrative embodiment of the present invention, the telecommunications session is a telephone call. However, it will be clear to those skilled in the art, after reading this disclosure, how to make and use alternative embodiments of the present invention in which the telecommunications session is any other type of telecommunications session, such as, for example, and without limitation, a video call, a chat conversation, teleconference, and others.

At task 320, availability detector 237 obtains a characteristic of the use of a software application that is running on computing device 160-1. In accordance with the illustrative embodiment of the present invention, the characteristic is obtained by computing device monitor 265 and then passed onto computing device monitor client 235 which forwards it to availability detector 237. Task 320 is further described in the discussion with respect to FIG. 4.

At task 330, availability detector 237 obtains a measurement of the use of one or more resources of computing device 160-1. In accordance with the illustrative embodiment of the present invention, the measurement is obtained by computing device monitor 265 and then passed onto computing device monitor client 235 which forwards it to availability detector 237. Task 330 is further described in the discussion with respect to FIG. 5.

At task 340, terminal 130-1 receives input from sensor 150-1. Task 340 is further described in the discussion with respect to FIG. 6.

At task 350, terminal 130-1 determines a characteristic of the invitation to participate in a telecommunications session. Task 350 is further described in the discussion with respect to FIG. 7

At task 360, terminal 130-1 determines whether to accept the invitation received at task 210. Task 360 is further described in the discussion with respect to FIG. 8.

At task 370, terminal 130-1 in a well known fashion transmits a response to the invitation to participate in a telecommunications session. In accordance with the illustrative embodiment of the present invention, the response is either an acceptance or a rejection. However, it will be clear to those skilled in the art, after reading this disclosure, how to make and use alternative embodiments of the present invention in which a message is transmitted to terminal 110 which identifies an action to be taken by the far-end party, such as, for example, and without limitation, call back later, use another medium of communication, and others. Furthermore, it will be clear to those skilled in the art, after reading this disclosure, how to make and use alternative embodiments of the present invention in which the message contains an indication of additional information concerning the telecommunications session, such as, for example, and without limitation, a preferred communication medium (e.g. voice, text, etc.), preferred alternative time to conduct a telecommunications session, and others.

And still furthermore, it will be clear to those skilled in the art, after reading this disclosure, how to make and use alternative embodiments of the present invention in which terminal 130-1 accepts the call and puts the far-end party on hold. The time for which the far-end party is put on hold can be determined according to an availability policy rule. In further embodiments, the present invention transmits a message to the far-end party indicating that he or she is being put on hold.

At task 380, terminal 130-1 executes an override sequence. The override sequence is executed when terminal 130-1 declines the invitation to participate in a telecommunications session. When this is the case, the user of terminal 110 is given the option to enter a password in order to override the decision of terminal 130-1 and force it to accept the incoming invitation. Task 380 is further described in the discussion with respect to FIG. 13.

FIG. 4 depicts a flowchart of the execution of the salient subtasks associated with the performance of task 320. It will be clear to those skilled in the art, after reading this disclosure, how to perform the tasks associated with FIG. 4 in a different order than represented or to perform one or more of the tasks concurrently. Furthermore, it will be clear to those skilled in the art, after reading this disclosure, how to make and use alternative embodiments of the present invention that omit one or more of the tasks.

At task 410, computing device monitor 265 determines the identity of a software application that is executing on computing device 160-1. In accordance with the illustrative embodiment of the present application, computing device monitor 265 determines the identity of the software application by examining log files that are recorded by the operating system of computing device 160-1. However, it will be clear to those skilled in the art, after reading this disclosure, how to make and use alternative embodiments of the present invention in which computing device monitor 265 uses alternative means to determine the identity of the application. In one alternative embodiment of the present invention, computing device monitor 265 identifies one or more active processes and matches information about the processes (e.g. process name, files associated with the process, etc.) to a specific application.

In another alternative embodiment of the present invention, computing device monitor 265 identifies patterns of resource consumption and matches these patterns that are known to be associated with specific applications. For example, and without limitation, the pattern of "85% CPU utilization, 85% memory use" may be associated with a computer game. Whereas the pattern of "25% CPU utilization, 60% cache miss rate" may be associated with a spreadsheet processor. It will be clear to those skilled in the art how to recognize and relate patterns of resource consumption to specific software applications.

At task 420, computing device monitor 265 determines the presence of a keyword in a file that is opened by a software application that is executing on computing device 160-1. In accordance with the illustrative embodiment of the present invention, the software application is a word processor, and the open file is a text document. However, it will be clear to those skilled in the art, after reading this disclosure, how to make and use alternative embodiments of the present invention in which the software application is any other software application that is capable of opening files (e.g. media player, another text editor, file compressing tool, etc.). Furthermore, it will be clear to those skilled in the art, after reading this disclosure, how to make and use alternative embodiments of the present invention in which the open files are of any other type (e.g. MP3, MPEG, JPEG, etc.)

In accordance with the illustrative embodiment of the present invention, computing device monitor 265 locates a document that has a lock placed on it and scans its content for the presence of a keyword. However, it will be clear to those skilled in the art, after reading this disclosure, how to make and use alternative embodiments of the present invention in which computing device monitor 265 locates documents that are open by using alternative means, such as, for example, and without limitation, monitoring system calls made by the software application, examining application log files which indicate what files are opened by the application. Moreover, in the alternative embodiments of the present invention in which the file is a media file, computing device monitor 265 uses voice recognition (or character/image recognition) technology to determine whether the keyword(s) are present in the file.

At task 430, computing device monitor 265 identifies an address to which a software application is (or was) connected. The address is an Internet domain name, but it will be clear to those skilled in the art, after reading this disclosure, how to make and use alternative embodiments of the present invention in which the uniform identifier (URI) is any type of identifier (e.g. Internet Protocol (IP) address, SIP uniform resource identifier (URI), etc.). Furthermore, the software application is an Internet browser, but it will be clear to those skilled in the art, after reading this disclosure, how to make and use alternative embodiments of the present invention in which the software application is any other type of software application (e.g. FTP client, streaming media player, a server, chat client, email client, etc.). In accordance with the illustrative embodiment of the present invention, the address is determined by examining log files that are recorded by the Internet browser. However, it will be clear to those skilled in the art, after reading this disclosure, how to make and use alternative embodiments of the present invention in which the address is identified by alternative means, such as, for example, and without limitation, by examining network traffic, by monitoring the storage of cookies and other tokens on computing device 160-1, etc.

Figure 5:
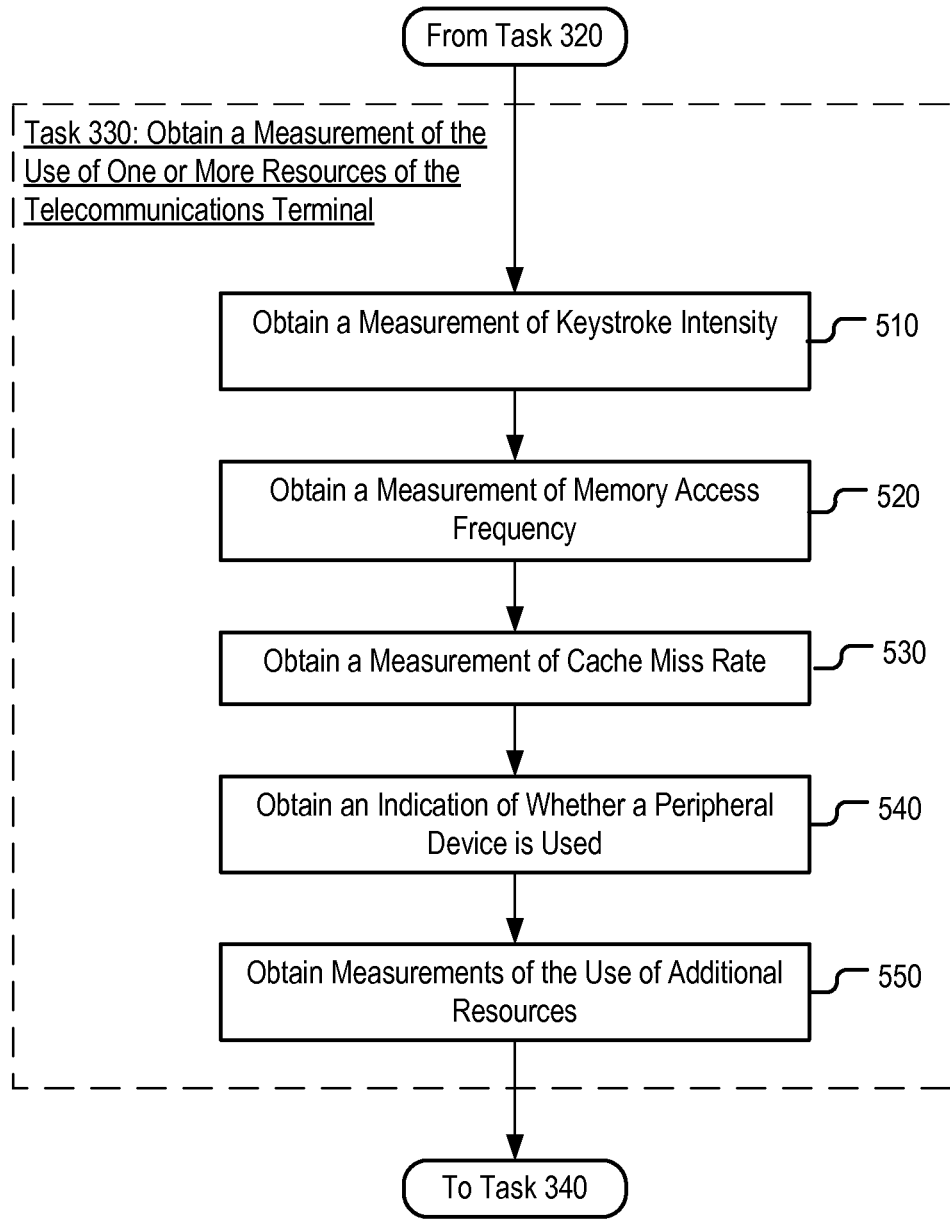
FIG. 5 depicts a flowchart of the execution of the salient subtasks associated with the performance of task 330.

FIG. 5 depicts a flowchart of the execution of the salient subtasks associated with the performance of task 330. It will be clear to those skilled in the art, after reading this disclosure, how to perform the tasks associated with FIG. 5 in a different order than represented or to perform one or more of the tasks concurrently. Furthermore, it will be clear to those skilled in the art, after reading this disclosure, how to make and use alternative embodiments of the present invention that omit one or more of the tasks.

The discussion with respect to FIG. 5 describes the taking of measurements of the use of resources of computing device 160-1. In accordance with the illustrative embodiment of the present invention, each measurement consists of five (5) samples taken four (4) seconds apart. However, it will be clear to those skilled in the art, after reading this disclosure, how to make and use alternative embodiments of the present invention in which any number of samples is taken (e.g. 1, 2, 3, 5, 100, 150, etc.). It will also be clear to those skilled in the art, after reading this disclosure, that each individual sample can be taken over any time window (i.e. the time period over which the data for an individual sample is collected can vary), such as, for example, and without limitation 1 second, 2 seconds, 3 seconds, 30 seconds, 1 minute, 15 minutes, 1 hour, etc. Furthermore, it will be clear to those skilled in the art that the time period between the different samples can be of any length (e.g. 1 second 10 seconds, 1 minute, 10 minutes, etc.). And still furthermore, it will be clear to those skilled in the art that the combination of number of samples, time over which each individual sample is taken, and time period between individual samples can be different for measurements of different resources.

At task 510, computing device monitor obtains a measurement of the keystroke rate for computing device 160-1. A keystroke rate is the rate at which the user of computing device 160-1 presses the keys on the keyboard of the computing device (e.g. 40 keys/minute, etc.).

At task 520, computing device monitor 265 obtains a measure of memory access frequency for computing device 160-1. In accordance with the illustrative embodiment of the present invention, the terminal measures the frequency at which information is requested from the permanent of storage of terminal 160-1. However, it will be clear to those skilled in the art, after reading this disclosure, how to make and use alternative embodiments of the present invention in which the terminal obtains alternative measurements, such as, for example, and without limitation, page fault rate, random access memory write rate, etc.

At task 530, computing device monitor 265 obtains a measurement of the cache miss rate for the processor of computing device 160-1.

At task 540, computing device monitor 265 determines whether a peripheral device is used by computing device 160-1. In accordance with the illustrative embodiment, the peripheral device is a scanner, but it will be clear to those skilled in the art, after reading this disclosure, how to make and use alternative embodiments of the present invention in which the use of another peripheral device is detected, such as, for example, and without limitation, printer, slide presentation remote control, microphone, audio speakers, video camera, headphones, etc.

At task 550, computing device monitor 265 obtains measurements of the use of additional hardware resources of terminal computing device 160-1. In accordance with the illustrative embodiment the present invention, computing device monitor 265 determines processor temperature, video card (or GPU) temperature, video card memory use, whether video card 3D acceleration is used, whether surround sound capabilities of a sound adapter are used, sound adapter utilization, processor temperature, processor, etc.

Figure 6:
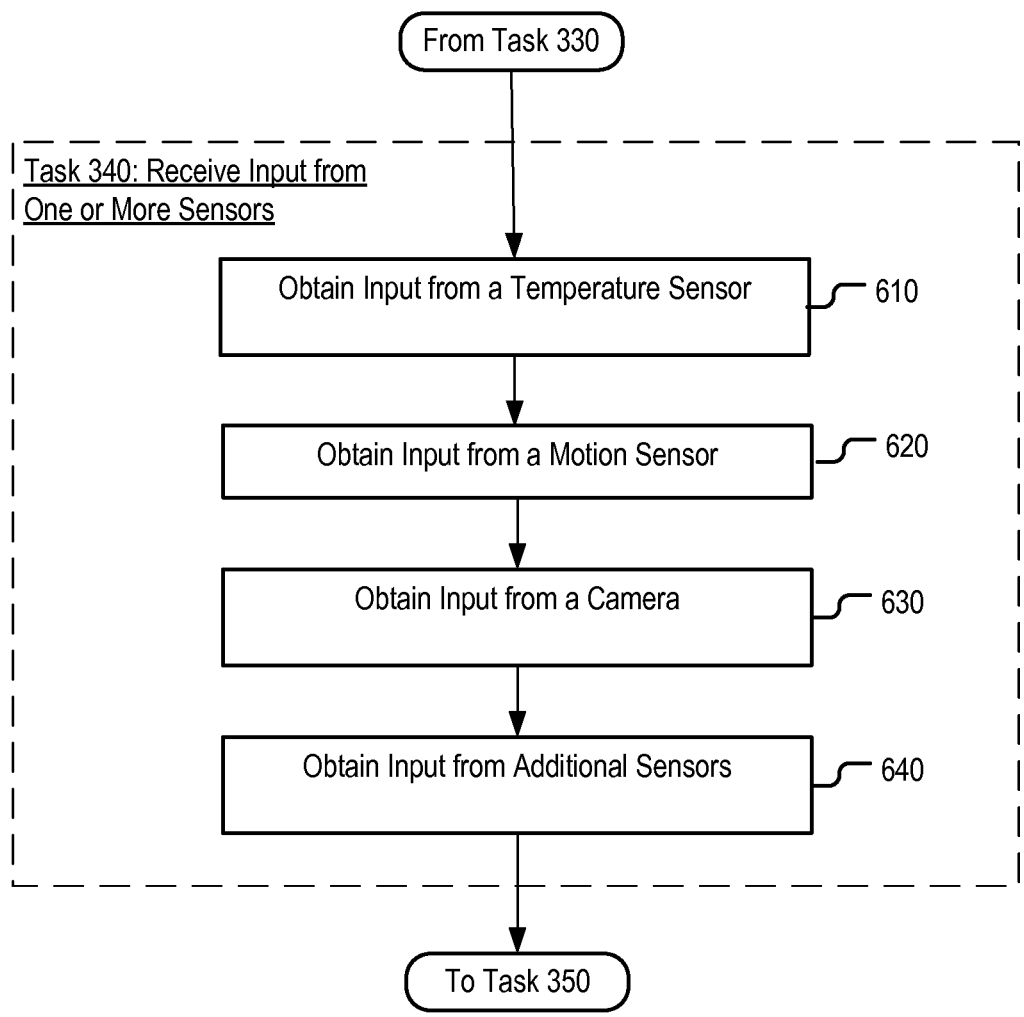
FIG. 6 depicts a flowchart of the execution of the salient subtasks associated with the performance of task 340.

FIG. 6 depicts a flowchart of the execution of the salient subtasks associated with the performance of task 240. It will be clear to those skilled in the art, after reading this disclosure, how to perform the tasks associated with FIG. 6 in a different order than represented or to perform one or more of the tasks concurrently. Furthermore, it will be clear to those skilled in the art, after reading this disclosure, how to make and use alternative embodiments of the present invention that omit one or more of the tasks.

The discussion with respect to FIG. 6 describes the taking of measurements from different sensors. In accordance with the illustrative embodiment of the present invention, each measurement consists of five (5) samples taken four (4) seconds apart. However, it will be clear to those skilled in the art, after reading this disclosure, how to make and use alternative embodiments of the present invention in which any number of samples is taken (e.g. 1, 2, 3, 5, 100, 150, etc.). It will also be clear to those skilled in the art, after reading this disclosure, that each individual sample can be taken over any time window (i.e. the time period over which the data for an individual sample is collected can vary), such as, for example, and without limitation, 1 second, 2 seconds, 3 seconds, 30 seconds, 1 minute, 15 minutes, 1 hour, etc. Furthermore, it will be clear to those skilled in the art that the time period between the different samples can be of any length (e.g. 1 second 10 seconds, 1 minute, 10 minutes, etc.). And still furthermore, it will be clear to those skilled in the art that the combination of: number of samples, time over which each individual sample is taken, and time period between individual samples can be different for measurements from different sensors.

At task 610, availability detector 237 obtains a temperature measurement from temperature sensor 251. It will be clear to those skilled in the art how to execute task 610.

At task 620, availability detector 237 obtains a measurement from motion sensor 252.

At task 630, availability detector 237 obtains input from camera 253. In accordance with the illustrative embodiment of the present invention, the camera input is used to determine whether a user is standing in the camera's range of vision. However it will be clear to those skilled in the art, after reading this disclosure, how to make and use alternative embodiments of the present invention in which availability detector 237 applies image recognition technologies such as, for example and without limitation, facial recognition, facial expression recognition, and gaze direction recognition.

At task 640, availability detector 237 obtains input from additional sensors, such as, for example, and without limitation, appliance sensors (i.e. sensors that detect whether a particular appliance such as a kitchen stove is running), barometric pressure sensors, humidity sensors, pressure sensors, sensors that measure physiological parameters (e.g. ECG, EEG, etc.), and others.

Figure 7:
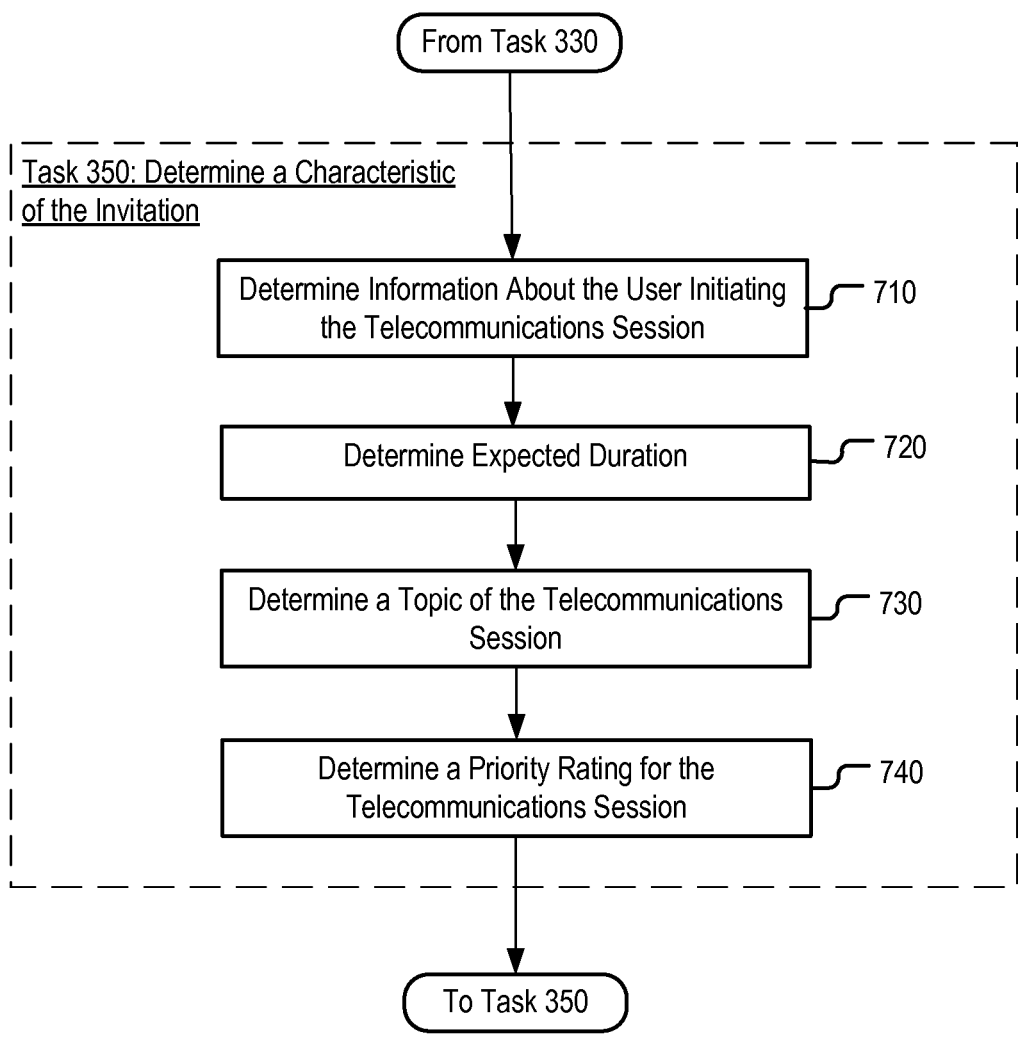
FIG. 7 depicts a flowchart of the execution of the salient subtasks associated with the performance of task 350.

FIG. 7 depicts a flowchart of the execution of the salient subtasks associated with the performance of task 350. It will be clear to those skilled in the art, after reading this disclosure, how to perform the tasks associated with FIG. 7 in a different order than represented or to perform one or more of the tasks concurrently. Furthermore, it will be clear to those skilled in the art, after reading this disclosure, how to make and use alternative embodiments of the present invention that omit one or more of the tasks.

At task 710, availability detector 237 obtains information about the user initiating the telecommunications session. In accordance with the illustrative embodiment of the present invention, availability detector 237 determines the endpoint identifier of the terminal from which the telecommunications session is initiated. However, it will be clear to those skilled in the art, after reading this disclosure, how to make and use alternative embodiments of the present invention in which availability detector 237 determines the identity of the person making the telephone call by using an identification technology, such as Caller ID or by doing a reverse telephone number lookup in a telephone directory.

It will also be clear to those skilled in the art, after reading this disclosure, how to make and use alternative embodiments of the present invention in which availability detector 237 determines additional information about the person initiating the telecommunications session, such as, for example, and without limitation, rank within a company (e.g. CEO, director of department, etc.), gender, age, employment status, social security number, etc. The alternative embodiments of the present invention obtain the additional information by performing a database search with a search key that is based on the endpoint identifier of terminal 110. However, it will be clear to those skilled in the art, after reading this disclosure, how to make and use further alternative embodiments of the present invention in which the additional information is contained in the invitation itself or contained in a separate message that is received by availability detector 237.

Furthermore, it will be clear to those skilled in the art, after reading this disclosure, how to make and use alternative embodiments of the present invention, in which a relationship between the user initiating the telecommunications session and the user of terminal 130-1 is obtained or determined (e.g. the caller is the supervisor of the user of terminal 130-1, the caller is a relative of the user of terminal 231-1, etc.). In some alternative embodiments of the present invention, the relationship information is received at terminal 130-1 along with the invitation to participate in a telecommunications session. In other embodiments of the present invention, the relationship between the caller and the user of terminal 130-1 is derived from the identity information of the caller and tables that relate the caller to the user (e.g. employee records, family records, etc.).

At task 720, availability detector 237 determines the expected duration of the telecommunications session. Availability detector 237 searches a call log for information about the duration of past telecommunications sessions between terminal 130-1 and terminal 110 and calculates the expected duration of the telecommunications session for which invitation is received. In accordance with the illustrative embodiment of the present invention, the expected duration is the average of the n most recent telecommunications sessions, where n is an integer.

Furthermore, it will be clear to those skilled in the art, after reading this disclosure, how to make and use alternative embodiments of the present invention in which the expected duration is contained in the invitation itself (e.g. the content of the ANI field or an equivalent is overwritten, etc.). And still furthermore, it will be clear to those skilled in the art, after reading this disclosure, how to make and use alternative embodiments of the present invention in which the expected duration is received at terminal 130-1 in a message that is separate from the invitation.

At task 730, availability detector 237 determines the topic of the telecommunications session. In accordance with the illustrative embodiment of the present invention, an indication of the topic is contained in the invitation itself (e.g. the content of the ANI field or an equivalent is overwritten, etc.). However, it will be clear to those skilled in the art, after reading this disclosure, how to make and use alternative embodiments of the present invention in which an indication of the topic is received in a message that is separate from the invitation.

At task 740, availability detector 237 determines a priority rating for the telecommunications session. In accordance with the illustrative embodiment of the present invention, one of three ratings is chosen: "important," "extremely important," and "not important." However, it will be clear to those skilled in the art, after reading this disclosure, how to make and use alternative embodiment of the present invention in which the space of possible ratings is either larger or smaller.

In accordance with the illustrative embodiment of the present invention, an indication of the priority rating is contained in the invitation itself (e.g. the content of the ANI field or an equivalent is overwritten, etc.). However, it will be clear to those skilled in the art, after reading this disclosure, how to make and use alternative embodiments of the present invention in which an indication of the priority rating is received in another message that is separate from the invitation. Furthermore, it will be clear to those skilled in the art, after reading this disclosure, how to make and use alternative embodiments of the present invention in which the importance rating is determined by availability detector 237 on the basis of information received at tasks 710 through 730 (e.g. if the CEO of a company call, the priority rating is set to "extremely important," the priority rating is set to "important" if the topic is "accounting," etc.).

Figure 8:
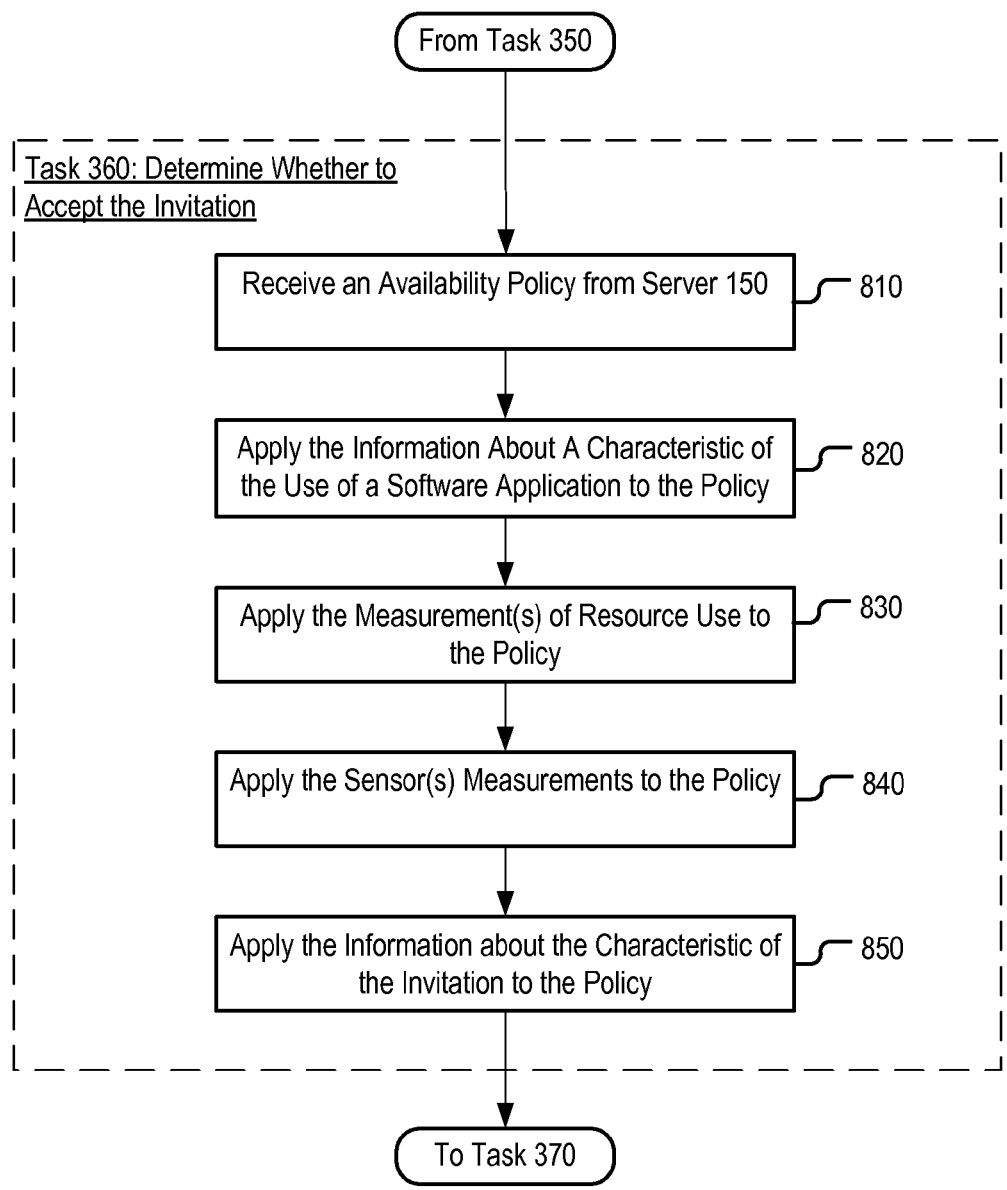
FIG. 8 depicts a flowchart of the execution of the salient subtasks associated with the performance of task 360.

FIG. 8 depicts a flowchart of the execution of the salient subtasks associated with the performance of task 360. It will be clear to those skilled in the art, after reading this disclosure, how to perform the tasks associated with FIG. 8 in a different order than represented or to perform one or more of the tasks concurrently. Furthermore, it will be clear to those skilled in the art, after reading this disclosure, how to make and use alternative embodiments of the present invention that omit one or more of the tasks.

At task 810, availability detector 237 receives an availability policy from server 150. As previously noted, for the purposes of this Specification, the term "availability policy" is defined as a set of one or more rules which determine when a user is available for telecommunications. In accordance with the illustrative embodiment of the present invention, the policy is received in an extensible markup language (XML) file, but it will be clear to those skilled in the art, after reading this disclosure, how to make and use alternative embodiments of the present invention in which the policy is represented in any other form, such as, for example, a text file, a sequence of numbers, etc. Although, in accordance with the illustrative embodiment of the present invention, the policy is obtained from a server, it will be clear to those skilled in the art, after reading this disclosure, how to make and use alternative embodiments of the present invention in which the policy is stored on terminal 130-1.

More specifically, at task 810, the present invention receives an availability policy which comprises four rules for determining whether a user is available. These rules are:
  i. "user is unavailable if the weighed sum of availability scores assigned to web sites which the user recently visited is below fifty-five (55),"
  ii. "user is unavailable if the weighted sum of the five most recent samples of the user's keystroke rate exceeds one-hundred and thirty (130),"
  iii. "user is unavailable if the temperature in the office of the user is below fifty-five-degrees Fahrenheit (55 F.)," and
  iv. "user is available if the CEO of a company calls."

In accordance with the illustrative embodiment of the present invention, the availability policy rules specify whether a user is to accept an incoming invitation to participate in a telecommunications session. However, it will be clear to those skilled in the art, after reading this disclosure, how to make and use alternative embodiments of the present invention in which the availability policy rules specify other aspects of a user's availability, such as, for example, and without limitation, an alternative communication medium, alternative time to call, time delay for which the far-end party is to be put on hold, etc.

In the alternative embodiments of the present invention in which availability policy rules are used to select a preferred medium of communication on which the user is available, the rules depend on one or more of a characteristic of the use of a software application that is executing on computing device 160-1, a measurement of the use of one or more resources of computing device 160-1, input from one or more sensors, and a characteristic of the invitation. Examples of such rules include:
  i. "notify far-end party that text is a preferred medium of communication if the keystroke rate of the user of computing device 160-1 exceeds eighty (80) characters per minute,"
  ii. "notify far-end party that voice is a preferred medium of communication if the user is using the chat component of a telephony application that is running on availability detector 237."

In the alternative embodiments of the present invention in which the incoming invitation to participate in a telecommunications session is accepted, but put on hold, the time period for which the session is held idle is determined in accordance with one or more availability policy rules. The availability policy rules in these alternative embodiments depend on one or more of: a characteristic of the use of a software application that is running on computing device 160-1, a measurement of the use of one or more resources of computing device 160-1, input from one or more sensors, and a characteristic of the invitation. Examples of such rules include:
  i. "put the session on hold for n minutes, if the measured keystroke rate is between fifty (50) and eighty (80) strokes per minute,"
  ii. "put the session on hold until the keystroke falls below a threshold (e.g. 50 keystrokes),"
  iii. "put the session on hold until a input from one or more sensors falls below a threshold (e.g. motion sensor indicates that a user has stopped moving intensely)," and
  vi. "put the session on hold until the user of computing device 160-1 stops using a specific software application."

It will be clear to those skilled in the art, after reading this disclosure, how to make and use alternative embodiments of the present invention in which tasks 330 through 360 are executed repeatedly, after the far-end party is put on hold, until availability detector 237 determines that a condition which determines whether a user is to be taken off hold has been fulfilled.

Furthermore, it will be clear to those skilled in the art, after reading this disclosure, how to make and use alternative embodiments of the present invention, in which terminal 130-1 initially declines the invitation to participate the telecommunications session from terminal 110, but continues to execute tasks 230 through 260 repeatedly until the user of terminal 130-1 becomes available, as determined according to an availability rule. When the user becomes available, terminal 130-1 initiates a new telecommunications session with terminal 110.

For example, and without limitation, in one alternative embodiment of the present invention, tasks 230 through 260 are executed until the user's keystroke intensity falls below a threshold, such as fifty keystrokes per minute. In this alternative embodiment of the present invention, the availability rule provides that a user is available if the user's keystroke rate is under fifty keystrokes per minute. Thus, when the user's keystroke rate falls below the threshold, terminal 130-1 initiates a new telecommunications session with terminal 110.

In the alternative embodiments of the present invention in which availability policy rules are used to determine an alternative time for the far end party to call, the rules depend on one or more of: a characteristic of the use of a software application that is executing on computing device 160-1, a measurement of the use of one or more resources of computing device 160-1, input from one or more sensors, and a characteristic of the invitation. Examples of such rules include:
  i. "if cache miss rate exceeds fifty percent (50%), ask far-end party to call back in 90 minutes,"
  ii. "if the movie player component of a multimedia player application is used, ask far-end party to call in a predetermined period of time (e.g. 120 minutes)."

In accordance with the alternative embodiments of the present invention, the call-back time period is provided in the policy rule used to determine availability. However, it will be clear to those skilled in the art, after reading this disclosure, how to make and use alternative embodiments of the present invention in which the call-back time period is determined according to appointment information that is stored on terminal 130-1 (e.g. information stored by calendar applications, etc.).

Although, in accordance with the illustrative embodiment of the present invention, the availability policy rules are neutral with respect to the time at which the telecommunications session is received or the medium of the telecommunications session, it will be clear to those skilled in the art, after reading this disclosure, how to make and use alternative embodiments of the present invention in which the rules depend on the time at which the invitation to participate on the telecommunications session is received or the medium of the telecommunications session. Examples of such rules include:

i. "user is unavailable if the invitation to participate in a telecommunications session is received within a specific time period;"
ii. "user is available if the medium for the telecommunications session is text;"
iii. user is unavailable if the medium for the telecommunications session is voice.

At task 820, availability detector 237 applies the first rule to the information obtained at task 320. Although, the first rule depends on the recent web site visits, it will be clear to those skilled in the art, after reading this disclosure, how to make and use alternative embodiments of the present invention in which the first rule depends on any type of information that is received at task 220 (e.g use of specific components of software, presence of keywords, etc.) Task 820 is further described in the discussion with respect to FIG. 9 and FIG. 10.

At task 830, availability detector 237 applies the second rule to the information obtained at task 330. Although, the second rule depends on keystroke intensity measurements, it will be clear to those skilled in the art, after reading this disclosure, how to make and use alternative embodiments of the present invention in which the second rule depends on any type of information that is received at task 330 (e.g. measurements of memory access rate, cache miss rate, information whether a peripheral device is used, etc.) Task 830 is further described in the discussion with respect to FIG. 11.

At task 840, availability detector 237 applies the third rule to the information that is received at task 340. Although, the third rule depends on a temperature measurement, it will be clear to those skilled in the art, after reading this disclosure, how to make and use alternative embodiments of the present invention in which the third rule depends on any type of information that is collected at task 340 (e.g. motion sensor input, camera input, etc.). Task 840 is further described in the discussion with respect to FIG. 12.

At task 850, availability detector 237 applies the fourth rule to the information that is obtained at task 350. In accordance with the rule, if the user which initiated the telecommunications session is the CEO of a company, availability detector 237 accepts the invitation. Although, the fourth rule depends on the position of the calling party within a company, it will be clear to those skilled in the art, after reading this disclosure, how to make and use alternative embodiments of the present invention in which the fourth rule depends on any information that is obtained at task 350. For example, and without limitation, such alternative rules include:

i. "user is always available if the priority rating of the invitation is "extremely important," and
ii. "the user is always available if the expected duration for the telecommunications session is less than a predetermined threshold (e.g. 5 minutes)."

It will also be clear to those skilled in the art, after reading this disclosure, how to make and use alternative embodiments of the present invention in which the rule depends on a relationship, which is determined at task 710, between the calling party and the user of terminal 130-1. For example, and without limitation, such rules include:

i. "user is always available if a relative of the user calls"
ii. "user is always available if someone who is higher up in the user's company calls."

Figure 9:
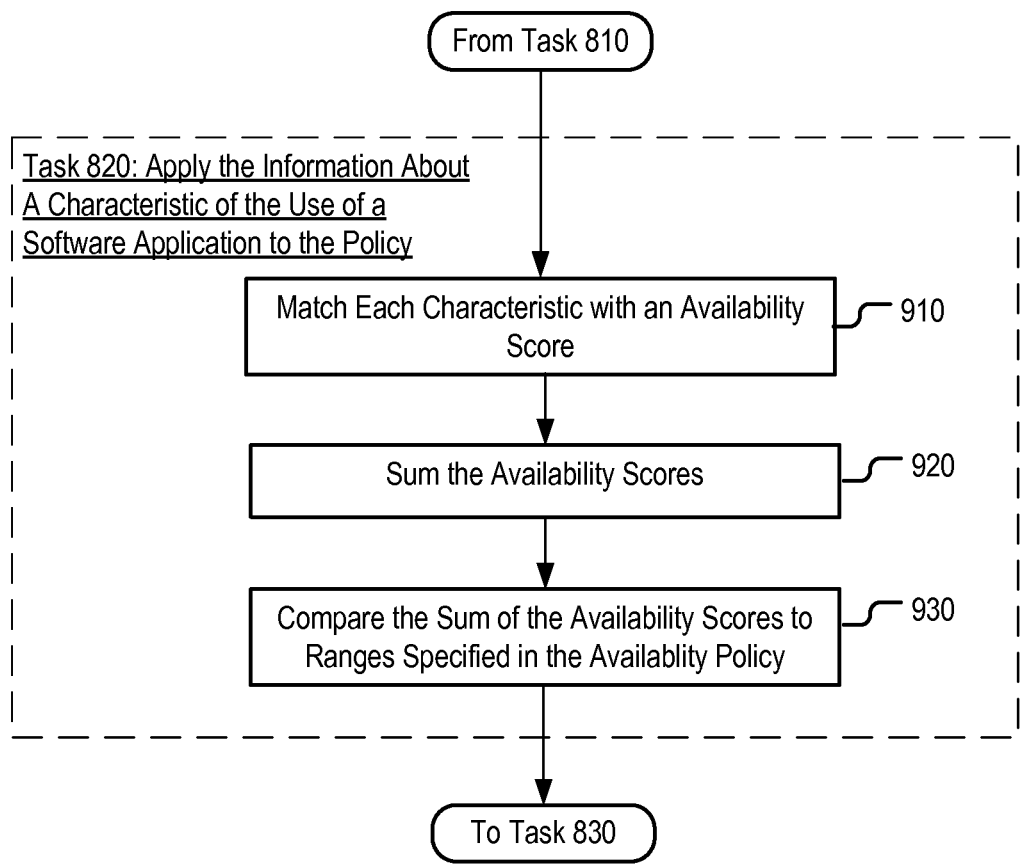
FIG. 9 depicts a flowchart of the execution of the salient subtasks associated with the performance of task 820.

FIG. 9 depicts a flowchart of the execution of the salient subtasks associated with the performance of task 820. It will be clear to those skilled in the art, after reading this disclosure, how to perform the tasks associated with FIG. 9 in a different order than represented or to perform one or more of the tasks concurrently. Furthermore, it will be clear to those skilled in the art, after reading this disclosure, how to make and use alternative embodiments of the present invention that omit one or more of the tasks.

At tasks 910 through 930, availability detector 237 applies the first policy rule received at task 810. The first policy rule provides that a user is unavailable if the weighed sum of availability scores assigned to web sites which the user recently visited is less than fifty-five (55).

Availability scores are numbers which are used in determining whether the user of terminal 130-1 is available to participate in telecommunications. In accordance with the illustrative embodiment of the present invention, the availability scores are contained in the indication of the policy received at task 810 (e.g. the XML file), however, those skilled in the art will readily recognize, after reading this disclosure, how to make and use alternative embodiments of the present invention in which the availability scores are separated from the availability policy, such as, for example, and without limitation, embodiments in which the availability scores are stored on terminal 130-1 or on a remote server.

At task 910, availability detector 237 matches a characteristic with an availability score. Furthermore, in accordance with a first illustrative embodiment of the present invention, the following set of availability scores is made available for uniform resource identifiers (URIs) that were visited by computing device 160-1:

TABLE 1

Availability Scores Assigned to Uniform Resource Identifiers

| Uniform Resource Identifier (URI) | Availability Score |
|---|---|
| Movies.com ™ | 10 |
| Bloomberg.com ™ | 40 |
| Internal_document_repository | 85 |

As noted, the availability score is an indication of the likelihood that the user of terminal 130-1 is not available to accept the incoming invitation. In accordance with the illustrative embodiment of the present invention, the magnitude of the availability score is inversely proportional to the probability that the user is available to respond to the invitation received at task 310. Furthermore, in accordance with the illustrative embodiment of the present invention, "Movies.com™" is assigned a low availability score. The rationale for assigning the low score is that Movies.com™ is a website that is usually viewed for personal entertainment. In contrast, the internal document repository, in this illustrative embodiment, is a document storage location which is used strictly for business. If the user is visiting the document repository, he or she is most likely to be engaged in performing tasks related to the user's employment. For this reason, the internal document repository is assigned a high availability score.

In accordance with an alternative embodiment of the present invention, the following availability scores are assigned to keywords that are found in documents that are opened for editing:

TABLE 2

Availability Scores Assigned to Keywords

| Keywords | Availability Score |
| --- | --- |
| "LOL" | 15 |
| "fiscal year" | 40 |
| "project deadline" | 85 |

In accordance with the second embodiment of the present invention, the word "LOL" is assigned a low priority score. "LOL" is an abbreviation for "laughing out loud" and is a common element of Internet slang. When this word is present in a document, the user of terminal 130-1 is likely engaged in a personal conversation. Consequently, the keyword "LOL" assigned a low availability score.

In accordance with the second alternative embodiment of the present invention, two types of documents are scanned for keywords by availability detector 237:
  i. documents which are open by the user of terminal 130-1 for editing, and
  ii. documents which are open by a software application for editing as a result of a user's interaction with the software application, such as a message log which is open as a consequence of a user sending an instant message, possibly, without the user being aware of its opening.

However, it will be clear to those skilled in the art, after reading this disclosure, how to make and use alternative embodiments of the present invention in which only one of the two types of documents is scanned.

At task 920, availability detector 237 calculates the sum of the availability scores identified at task 910. It will be clear to those skilled in the art, after reading this disclosure, how to make and use alternative embodiments of the present invention in which availability detector 237 calculates an alternative number, such as, for example, and without limitation, a weighted sum, weighted average, the average of the scores, and others.

At task 930, availability detector 237 matches the calculated sum to a predetermined range defined in the policy received at task 810. In accordance with the illustrative embodiment of the present invention, the policy provides that if the sum is less than fifty-five (55), the user of terminal 130-1 is available to accept the invitation to participate in a telecommunications session.

Figure 10:
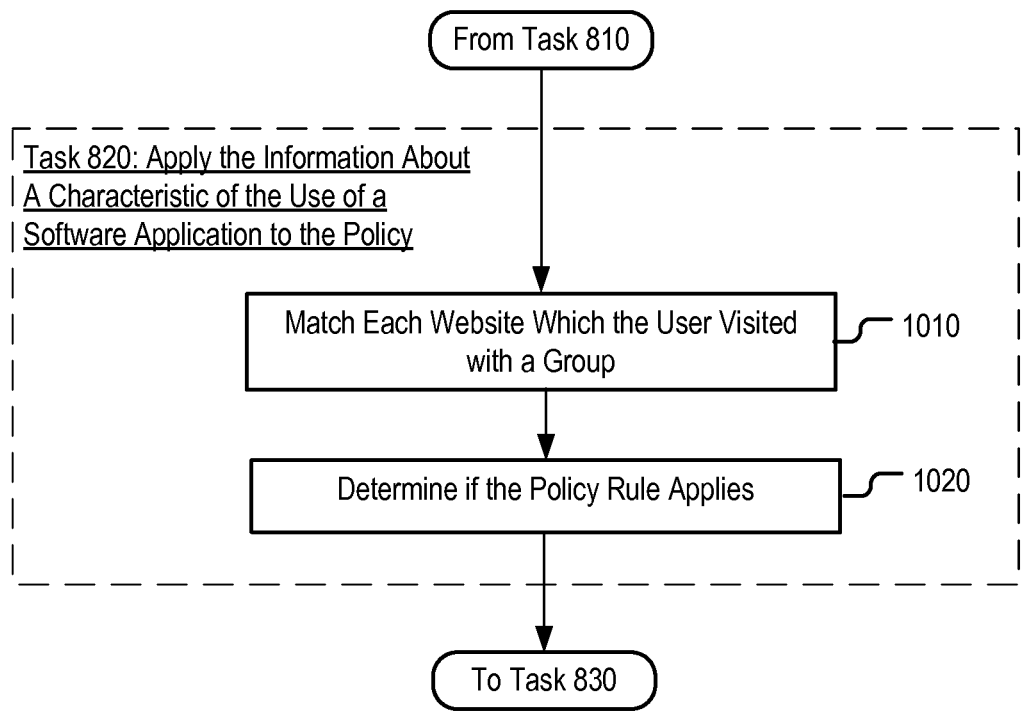
FIG. 10 depicts a flowchart of the execution of the salient subtasks associated with the performance of task 820 as performed by another illustrative embodiment of the present invention.

FIG. 10 depicts a flowchart of the execution of the salient subtasks associated with the performance of task 820 as performed by another illustrative embodiment of the present invention. It will be clear to those skilled in the art, after reading this disclosure, how to perform the tasks associated with FIG. 10 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1010 and 1020, availability detector 237 applies a policy rule. The policy rule provides that a user is unavailable if the number of websites from a "business" group, which the user visited, is more than or equal to the number of visited websites from a "personal entertainment" group.

In accordance with this illustrative embodiment of the present invention, the websites visited are classified into groups. The group definitions are contained in the policy received at task 810 (e.g. the XML file), but those skilled in the art will readily recognize, after reading this disclosure, how to make and use alternative embodiments of the present invention in which the group definitions are stored on terminal 130-1 or on a remote server.

At task 1010, availability detector 237 determines the groups for the last three web sites that were most recently visited by an Internet browser executing on computing device 160-1. The three websites are "Movies.com™," "Bloomberg.com™," and "internal document repository." The group definitions for the illustrative embodiment of the present invention are listed below:

TABLE 3

Web Site Group Definitions

| Business Websites | Entertainment Websites | News Websites |
| --- | --- | --- |
| Internal document repository | Youtube.com ™ | Bloomberg.com ™ |
| Corporation web site | Movies.com ™ | Cnn.com ™ |
| A client web site | Netflix.com ™ | News.com ™ |
| Another client's website | Cinema.com ™ | bbc.com ™ |

It will be clear to those skilled in the art, after reading this disclosure, how to make and use alternative embodiments of the present invention in which the group definitions are different. Those skilled in the art will readily recognize, after reading this disclosure that the group definitions depend on the application for which the invention is used.

At task 1020, availability detector 237 determines whether the policy rule applies. Since Movies.com™ belongs to the entertainment group, the internal document repository belongs to the business group, and Bloomberg.com™ belongs to neither of the "business" and "entertainment groups," the number of "business" websites visited by the user is more than or equal to the number of "entertainment" web sites. Therefore, in accordance with the availability policy rule of this embodiment, the user is found available to participate in a telecommunications session.

Figure 11:
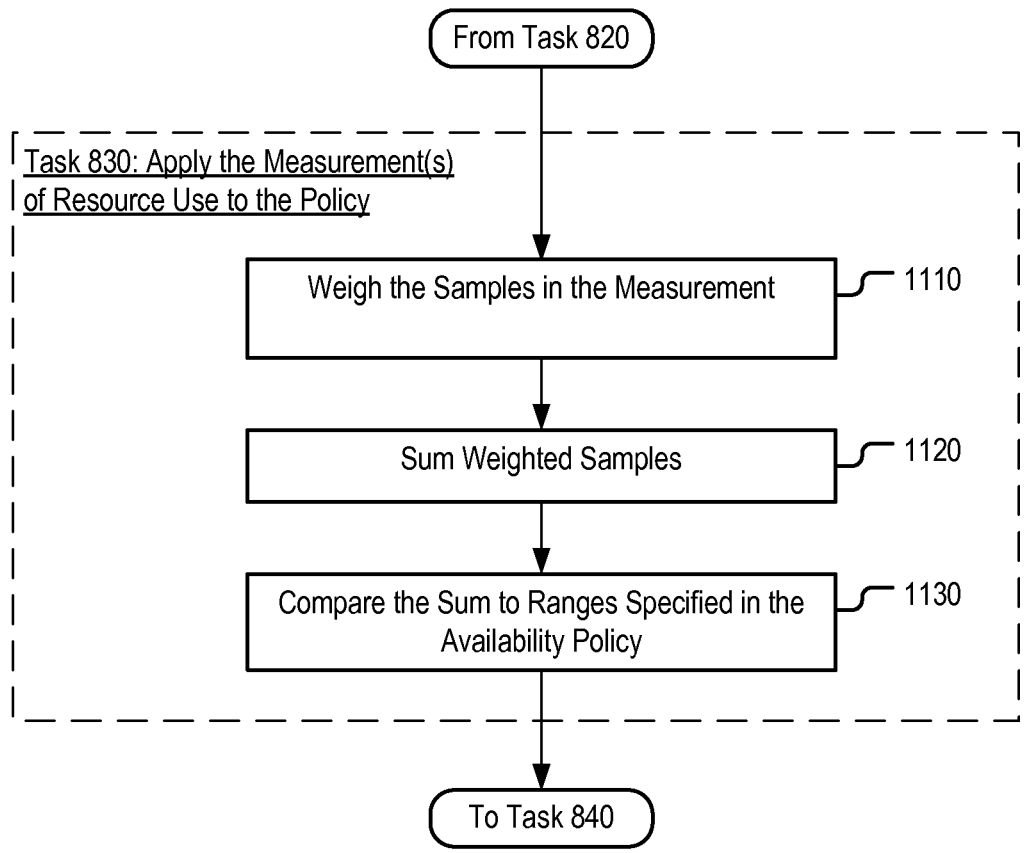
FIG. 11 depicts a flowchart of the execution of the salient subtasks associated with the performance of task 830.

FIG. 11 depicts a flowchart of the execution of the salient subtasks associated with the performance of task 830. It will be clear to those skilled in the art, after reading this disclosure, how to perform the tasks associated with FIG. 11 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1110 through 1130, availability detector 237 applies the second policy rule received at task 810 to the information received at task 330. The second policy rule provides that a user is unavailable if the weighted sum of the five most recent samples of the user's keystroke rate exceeds one-hundred and thirty (130).

At task 1110, availability detector 237 weights the samples in the measurements of the use of resources of computing device 160-1 which were obtained at task 330. In accordance with the illustrative embodiment of the present invention, availability detector 237 receives a measurement of the rate at which keys on its keyboard are struck (i.e. keystroke rate).

Availability detector 237 receives the data samples contained in the first two rows of Table 4:

TABLE 4

Keystroke Samples and Corresponding Weight Values

| | Sample (keystrokes/minute) | | | | |
|---|---|---|---|---|---|
| | 45 | 80 | 55 | 32 | 65 |
| Time at Which the Sample is Taken | $t_0$ | $t_1$ | $t_2$ | $t_3$ | $t_4$ |
| Weight Coefficient | 1 | .85 | .75 | .60 | .45 |

In accordance with the illustrative embodiment of the present invention, each sample is multiplied to the weight coefficient in order to derive the weighted value of this sample. The samples are weighted according to the time at which they are taken (e.g. the more recent samples are weighted less). It will be clear to those skilled in the art how to assign appropriate weight values. Furthermore, it will be clear to those skilled in the art, after reading this disclosure, how to make and use alternative embodiments of the present invention in which the samples are not weighted.

At task 1120, availability detector 237 calculates the sum of the weighted samples.

At task 1130, availability detector 237 matches the calculated sum to a predetermined range defined in the policy received at task 810. In accordance with the illustrative embodiment of the present invention, the policy provides that if the sum of the weighted keystroke rate samples is less than 130, the user of terminal 130-1 is available to accept the invitation to participate in a telecommunications session. Although, the policy is based on a plurality of keystroke rate samples, it will be clear to those skilled in the art, after reading this disclosure, how to make and use alternative embodiments of the present invention in which the policy depends on a single sample (e.g. "user is unavailable if keystroke rate is greater than eighty (80) characters per minute), on the weighted average of the samples or any other combination of the samples.

Although, the policy rule of the illustrative embodiment of the present invention depends on keystroke rate, it will be clear to those skilled in the art, after reading this disclosure, how to make and use alternative embodiments of the present invention in which the availability policy rule depends on the use of other resources measured at task 230 (e.g. both keystroke rate and cache miss rate, etc.). Examples of such rules are:

i. "user is unavailable when cache miss rate exceeds fifty percent (50%);"
ii. "user is available if less than ten (10) read requests to a permanent storage device are made in the past minute;"
iii. "user is unavailable if a scanner connected to computing device 160-1 is being used at the time at which the invitation to participate in a telecommunications session is received."

It will be clear to those skilled in the art, after reading this disclosure how to make and use alternative embodiments of the present invention in which the ranges for availability and unavailability differ from the illustrative embodiment. It will be clear to those skilled in the art, after reading this disclosure, how to assign values to the ranges. Furthermore, it will be clear to those skilled in the art, after reading this disclosure, how to make and use alternative embodiments of the present invention, in which a third range is specified and when the sum falls into the third range, a message is transmitted from terminal 130-1 to terminal 110 asking the user of terminal 110 to call back in a predetermined period of time (e.g. 30 minutes).

Figure 12:
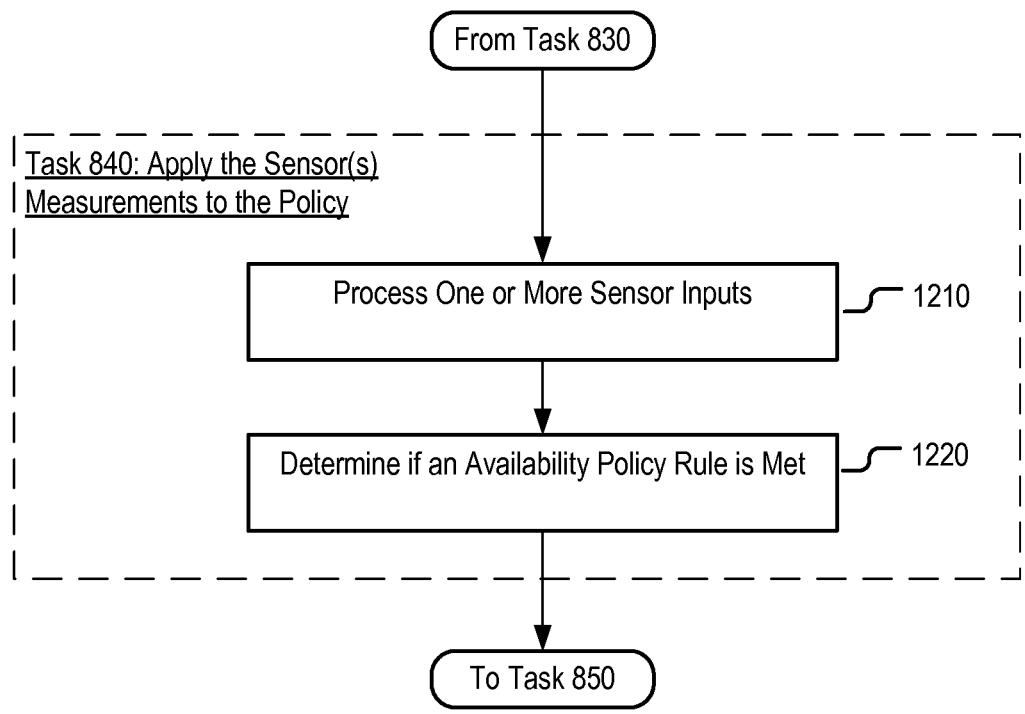
FIG. 12 depicts a flowchart of the execution of the salient subtasks associated with the performance of task 840.

FIG. 12 depicts a flowchart of the execution of the salient subtasks associated with the performance of task 840. It will be clear to those skilled in the art, after reading this disclosure, how to perform the tasks associated with FIG. 12 in a different order than represented or to perform one or more of the tasks concurrently. Furthermore, it will be clear to those skilled in the art, after reading this disclosure, how to make and use alternative embodiments of the present invention that omit one or more of the tasks.

At tasks 1210 through 1230, availability detector 237 applies the third policy rule received at task 810 to the information received at task 340. The third policy rule provides that a user is unavailable if the temperature in the office of the user is below fifty-five degrees Fahrenheit (55 F.).

At task 1210, availability detector 237 processes the sensor input received at task 240. In accordance with the illustrative embodiment of the present invention, availability detector 237 digitizes (when analog signal is received) and normalizes the sensor data received at task 340. Although, in accordance with the illustrative embodiment of the present invention, input from a temperature sensor is processed, it will be clear to those skilled in the art, after reading this disclosure, how to make and use alternative embodiments of the present invention in which input from other sensors (e.g. motion sensors, physiological sensors, humidity sensors, etc.) is processed in the same fashion.

In accordance with one alternative embodiment of the present invention, availability detector 237 processes the camera input received at task 630 to determine the mood of the user. Specifically, the terminal uses a mood detector that employs facial recognition. However, it will be clear to those skilled in the art, after reading this disclosure, how to make and use alternative embodiments of the present invention in which input from physiological sensors (e.g. ECG and ECG) is also used in assessing the mood of the user of terminal 130-1.

At task 1220, availability detector 237 determines whether the input from a temperature sensor received at task 340 indicates that the temperature is below fifty-five degrees Fahrenheit (55 F.).

In accordance with the alternative embodiment of the present invention, availability detector 237 applies the results from the mood detection to a policy which relates users' mood to their availability. Furthermore, in accordance with the alternative embodiment of the present invention, the policy provides that the incoming invitation should be accepted only when the mood detection concludes that the user of terminal 130-1 is in a positive mood.

Figure 13:
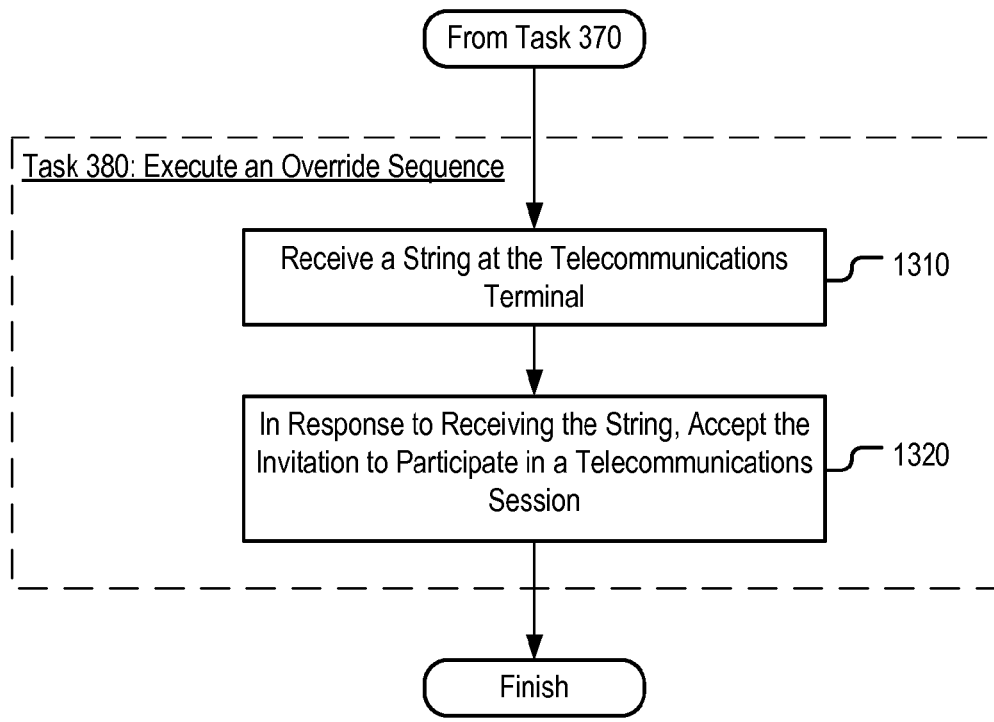
FIG. 13 depicts a flowchart of the execution of the salient subtasks associated with the performance of task 380.

FIG. 13 depicts a flowchart of the execution of the salient subtasks associated with the performance of task 380. It will be clear to those skilled in the art, after reading this disclosure, how to perform the tasks associated with FIG. 13 in a different order than represented or to perform one or more of the tasks concurrently. Furthermore, it will be clear to those skilled in the art, after reading this disclosure, how to make and use alternative embodiments of the present invention that omit one or more of the tasks.

At task 1310, terminal 130-1 receives a string from terminal 110. In accordance with the illustrative embodiment of the present invention, the string is alphanumerical, but it will be clear to those skilled in the art, after reading this disclosure, that the string can be of any type (e.g. numerical, etc.)

At task 1320, availability detector 237 compares the received to the string to a second string which is stored on terminal 130-1. If the two strings match, availability detector 237 causes terminal 130-1 to accept the invitation received at task 310. It will be clear to those skilled in the art, after reading this disclosure, how to make and use alternative embodiments of the present invention in which the string is stored on a remote server and not on terminal 130-1. Furthermore, it will be clear to those skilled in the art, after reading this disclosure, how to make and use alternative embodiments of the present invention in which the second string is specified by the policy received at task 810. And still furthermore, it will be clear to those skilled in the art, after reading this disclosure, how to make and use alternative embodiments of the present invention in which the policy received at task 810 provides whether availability detector 237 should accept the call even if the two strings match (i.e. the policy provides whether the override component of the present invention is enabled).

It is to be understood that the disclosure teaches just examples of the illustrative embodiments and that many variations of the invention can easily be devised by those skilled in the art after reading this disclosure and that the scope of the present invention is to be determined by the following claims.

What is claimed is:

1. A method comprising:
   receiving, at a communications terminal, an invitation to participate in a communications session;
   obtaining, at the communications terminal, a first measurement of a central processing unit utilization rate of a computing device that is different from the communications terminal;
   obtaining, at the communications terminal, a second measurement of memory use of the computing device; and
   transmitting, from the communications terminal, a response to the invitation, wherein the response depends on a pattern represented by the first measurement and the second measurement.

2. The method of claim 1, wherein the computing device is associated with the communications terminal.

3. The method of claim 1, further comprising:
   receiving, at the communications terminal, an indication of an availability policy,
   wherein the response to the invitation further depends on the availability policy.

4. The method of claim 1, wherein the response further depends on a characteristic of the invitation.

5. The method of claim 1, wherein the response indicates a refusal to accept the invitation, the method further comprising:
   receiving a string at the communications terminal; and
   in response to the receiving of the string, accepting the invitation to participate in the communications session.

6. The method of claim 1, further comprising:
   identifying, at the communications terminal, an alternative time to conduct the communications session, wherein the response contains an indication of the alternative time.

7. The method of claim 1, the method further comprising:
   obtaining, at the communications terminal, a third measurement of the computing device, wherein the third measurement is of one from among keystroke intensity, memory access frequency, cache miss rate, peripheral device use, processor temperature, video card temperature, video card memory use, 3D video acceleration use, and sound adapter use, and wherein the pattern is further represented by the third measurement.

8. The method of claim 1, further comprising:
   obtaining, at the communications terminal, a characteristic of use of a software application executing on the computing device,
   wherein the response further depends on the characteristic of use.

9. The method of claim 8,
   wherein the characteristic is a uniform resource identifier to which the software application established a connection.

10. The method of claim 8, wherein the characteristic is presence of a keyword.

11. The method of claim 8, wherein the characteristic is access permission for a document that is open for editing by the software application.

12. The method of claim 8, wherein the response is a rejection, and the method further comprising:
    obtaining, at the communications terminal, a second characteristic of use of the software application; and
    initiating a communications session from the communications terminal, wherein the communications session is initiated when the second characteristic meets a criterion.

13. The method of claim 8, further comprising identifying, at the communications terminal, an alternative communications medium, wherein the alternative communications medium is identified on a basis of the characteristic of use of the software application, and wherein the response to the invitation to participate in the communications session contains an indication of the alternative communications medium.

14. A system comprising:
    a processor; and
    a computer-readable storage medium storing instructions which, when executed by the processor, cause the processor to perform operations comprising:
       receiving, at a communications terminal, an invitation to participate in a communications session;
       obtaining, at the communications terminal, a first measurement of a central processing unit utilization rate of a computing device that is different from the communications terminal;
       obtaining, at the communications terminal, a second measurement of memory use of the computing device; and
       transmitting, from the communications terminal, a response to the invitation, wherein the response depends on a pattern represented by the first measurement and the second measurement.

15. The system of claim 14, the computer-readable storage medium storing additional instructions which, when executed by the processor, cause the processor to perform further operations comprising:
    receiving, at the communications terminal, an indication of an availability policy,
    wherein the response to the invitation further depends on the availability policy.

16. A computer-readable storage device storing instructions which, when executed by a processor, cause the processor to perform operations comprising:
    receiving, at a communications terminal, an invitation to participate in a communications session;

obtaining, at the communications terminal, a first measurement of a central processing unit utilization rate of a computing device that is different from the communications terminal;

obtaining, at the communications terminal, a second measurement of memory use of the computing device; and transmitting, from the communications terminal, a response to the invitation, wherein the response depends on a pattern represented by the first measurement and the second measurement.

17. The computer-readable storage device of claim 16, storing additional instructions which, when executed by the processor, cause the processor to perform further operations comprising:

obtaining, at the communications terminal, a third measurement of the computing device, wherein the third measurement is of one of keystroke intensity, memory access frequency, cache miss rate, peripheral device use, processor temperature, video card temperature, video card memory use, 3D video acceleration use, and sound adapter use, and wherein the pattern is further represented by the third measurement.

18. The computer-readable storage device of claim 16, wherein the computing device is associated with the communications terminal.

19. The computer-readable storage device of claim 16, storing additional instructions which, when executed by the processor, cause the processor to perform further operations comprising:

receiving, at the communications terminal, an indication of an availability policy, wherein the response to the invitation further depends on the availability policy.

20. The computer-readable storage device of claim 16, wherein the response further depends on a characteristic of the invitation.

* * * * *